United States Patent [19]
Goldman

[11] Patent Number: 4,758,163
[45] Date of Patent: Jul. 19, 1988

[54] ENDODONTIC MATERIAL AND METHOD

[75] Inventor: Melvin Goldman, Worcester, Mass.

[73] Assignee: Trustees of Tufts College, Medford, Mass.

[21] Appl. No.: 3,122

[22] Filed: Jan. 14, 1987

Related U.S. Application Data

[63] Continuation of Ser. No. 543,314, Oct. 19, 1983, Pat. No. 4,645,457.

[51] Int. Cl.⁴ .............................................. A61C 5/00
[52] U.S. Cl. .................................................. 433/229
[58] Field of Search ........................................ 433/229

[56] References Cited

U.S. PATENT DOCUMENTS

| | | | |
|---|---|---|---|
| 3,539,533 | 11/1970 | Lee, II et al. | 106/35 X |
| 3,835,090 | 9/1974 | Gander et al. | 106/35 X |
| 3,926,906 | 12/1975 | Lee, II et al. | 106/35 X |
| 3,928,280 | 12/1975 | Erickson et al. | 106/35 X |
| 4,102,856 | 7/1978 | Lee, Jr. | 106/35 X |
| 4,148,988 | 4/1979 | Masuhara et al. | 106/35 X |
| 4,239,489 | 12/1980 | Ellman et al. | 433/220 |
| 4,362,511 | 12/1982 | Jacklich | 433/220 |
| 4,381,918 | 5/1983 | Ehinford | 106/35 X |
| 4,435,160 | 3/1984 | Randklev | 106/35 X |

FOREIGN PATENT DOCUMENTS

| | | | |
|---|---|---|---|
| 745982 | 2/1933 | France | 433/220 |
| 899338 | 5/1945 | France | 433/220 |
| 91878 | 6/1958 | Norway | 433/221 |

OTHER PUBLICATIONS

J. Endod., 1(10), 324–44 (1975).
J. Endod., 2(9), 261–66 (1976).
J. Endod., 6(11), 815–22 (1980).
J. Pros. Dent., 39(2), 169–72 (1978).
J. Dent. Res., 44(5), 895–902, Sep.–Oct. (1965).
Int'l Dent. Journal, 35:160–165 (1985).
J. Endod., 1(4), 127–35 (1975).
J. Endod., 1(7), 238–42 (1975).
J. Endod., 5(11), 328–35 (1975).
Oral Surg., 52(2), 197–204 (1981).
J. Dent. Res., 60(B), 1211 (1981) (See Abstract #53).
Scard, J. Dent. Res., 88(5), 397 (1980).
J. Endod., 5(a), 258–265 (1979).
Oral Surg., 48(1), 79–83 (1979).
J. Endod., 8(11), 487–492 (1982).
J. Endod., 9(4), 137–142 (1983).
Submitted for Publication, "The Effect of the Smeared Layer on the Tensile Strength of Posts . . . ".

Primary Examiner—Nancy A. B. Swisher
Attorney, Agent, or Firm—Blodgett & Blodgett

[57] ABSTRACT

Kit for use in restructuring a tooth by attaching a crown replacement on an endodontically treated tooth. A plugger is provided to heat and remove gutta percha, a burr to prepare a site consisting of a bore and counterbore, and at least one drill for final preparation of the bore. A post is provided corresponding in size to the drill and a chelating agent for flushing the site. An organic flushing agent is provided for flushing the site, as well as a cementing agent consisting of an unfilled resin and catalyst for application to the site within which the post is seated. A spiral apparatus is provided for the said application of the cementing medium in the prepared site and a composite resin is provided to fabricate a core and a crown form around the post.

13 Claims, 1 Drawing Sheet

ENDODONTIC MATERIAL AND METHOD

This is a continuation of co-pending application Ser. No. 543,314, filed on Oct. 19, 1983, now U.S. Pat. No. 4,645,457, on Feb. 24, 1987.

BACKGROUND OF THE INVENTION

1. Field of the Invention

The present invention relates to compositions and methods of use of materials in endodontology, more specifically to the combined use of ethylenediaminotetraacetic acid (EDTA) and sodium hypochlorite to prepare an endodontically treated tooth for crown replacement by the post and cement method.

2. Setting for the Invention

It has previously been known that a post may be placed in an endodontically treated tooth to retain a superstructure that replaces missing coronal tooth structure. Thus, the retention of the crown is greatly enhanced. Posts have been employed in refabrication for several centuries. Over the years, posts of varying configuration have been cemented with various cements with varying degrees of success and acceptance. Presently the two most popular cements are zinc oxyphosphate cement, which has been used since 1900, and polycarboxylate cement introduced in 1968.

Placement of an artificial crown requires that the remaining structure of the tooth be properly prepared by instrumentation after the root canal space has been cleaned, shaped and filled. Generally, an interior space is machined into the root canal. Irrigation usually accompanies instrumentation and serves to cool and lubricate the cutting tool while flushing removed material away from the machined site. Once the root canal is prepared a post of appropriate size and shape is cemented into the canal. After the cement has sufficiently hardened, a mass around the top of the post is built-up of various substances, called a core. Generally, preformed crowns are available and have a hollow area to accept such a build-up mass. These are placed as a temporary cover until a final crown has been made. This crown is placed upon the prepared tooth structure and bonded to the tooth and core using various cements.

In the past few years, there has been much discussion about the inability of chemomechanical procedures to thoroughly remove all the cellular debris within the root canal space. Silicone models are used to demonstrate the great irregularity and complexity of the root canal space. They illustrate that even mechanically well-prepared canals harbored areas that were never contacted by endodontic instruments. Scanning electron microscope (SEM) studies of the effects of mechanical preparation revealed that, regardless of the technique used, often pulp tissue remained and areas of the canal walls were not instrumented. See Mizrahi et al., "A scanning electron microscopic study of the efficacy of various endodontic instruments", *J. Endod.* 1(10): 324–33, (1975); Moodnick et al., "Efficacy of Biomechanical instrumentation: a scanning electron microscopic study," *J. Endod.* 2(9): 261–66, (1976); Bolanos and Jensen, "Scanning electron microscope comparisons of the efficacy of various methods of root canal preparation," *J. Endod.* 6(11): 815–22, (1980). In addition, other studies using the SEM found that many of the commonly used irrigating solutions were also ineffective in completely removing hard and soft tissue debris, especially in the apical portion of the canal. See Baker et. al., "Scanning electron microscopic study of the efficacy of various irrigating solutions," *J. Endod.* 1(4): 127–35, (1975); McComb and Smith, "A preliminary scanning electron microscopic study of root canals after endodontic procedures," *J. Endod.* 1(7): 238–42, (1975); Rubin et. al., "The effect of instrumentation and flushing of freshly extracted teeth in endodontic therapy: a scanning electron microscopic study," *J. Endod.* 5(11): 328–35, (1979). These results show that currently accepted methods of chemomechanical preparation were inadequate in preparing a debris-free canal.

Thus, emphasis has been placed on improving the manufacture of endodontic instruments and developing more effective irrigation techniques and endodontic materials.

Since instrumentation is not effective in cleaning the entire canal, the solutions used should help remove pulp tissue remnants, necrotic debris and bacteria remaining in the prepared root canal space without irritating the periapical tissues.

Investigators have also described a sludge or smeared layer that exists on portion of the canal walls. This appears as an amorphous layer on the canal wall that obstructs the dentinal tubules. It was recently demonstrated that the smeared layer is primarily calcific in nature and is created by instrumentation. See Goldman et al., "The efficacy of several Endodontic irrigating solutions: a scanning electron microscopic study," *Oral Surg.* 52(2): 199–204, (1981).

The smeared layer blocks the dentinal tubules. A recent study has shown that this calcific layer reduced the permeability of dentin in vitro by more than forty percent. See Dippel et al., "Influence of the smeared layer and intermediary base materials on the permeability of dentin," *J. Dent. Res.* 60(B):1211, (1981).

Therefore, even well-instrumented canals could contain organic debris such as pulp tissue as well as inorganic debris such as a smeared layer. Recent investigations raised the question of removing both layers. See Wayman et al., supra and Koskinen et al., "Appearance of the chemically treated root canal walls in the scanning electron microscope," *Scand. J. Dent. Res.* 88(5):397, (1980). However, those attempts were unsuccessful.

SUMMARY OF THE INVENTION

It has now been found that instrumented canals can be cleaned more effectively by using one solution to remove organic debris and another to remove inorganic debris, and when the smeared layer is removed and the dentinal tubules are exposed, a cementing medium which has great compressive strength can flow into the open tubules, around the post and can provide a greatly enhanced tensile strength and is therefore a significant improvement over previous methods.

The present invention presents a novel solution to the aforesaid problems by providing a method of placing a crown replacement on a tooth that provides enhanced foundation strength and security. The machined or prepared area is washed first with a chelating agent and then flushed with an organic solvent to remove debris and expose the dentinal tubules. Secondly, the post and cap are placed with an appropriate cementing medium. The present invention overcomes the disadvantages of the previous methods by providing a method of endodontic preparation and placement that significantly improves retention of coronal structures.

The invention herein comprises methods and products for attaching a crown replacement on an endodontically treated tooth. The superior surface of the tooth is shaped to receive the base of the crown replacement and an interior space is machined into the root canal to accept placement of a post. The instrumented area is then flushed with a chelating agent followed by an organic solvent. A cementing medium having great compressive strength is placed around a post fitted into the cavity. After the cement has set, a quantity filler material is placed around the remaining exposed part of the post. This post forms the support for the crown replacement. If desired, a preformed crown replacement may be placed over the cemented structure until a permanent crown can be made.

DESCRIPTION OF THE DRAWING

This invention can be more clearly understood by referring to the accompanying drawings wherein.

DETAILED DESCRIPTION OF THE INVENTION

In one embodiment of the present invention a tooth lacking a substantial coronal portion is prepared for crown replacement by cleaning the root canal, forming a bore for placement of a post and forming a counterbore to aid in post retention. During or following instrumentation a chelating agent and then an organic solvent are used as a flush to prepare the instrumented surfaces for crown replacement. Following the surface cleaning, the post is inserted and cemented in place. A core is formed around the post with a build-up substance and the crown is fitted in the proper position. Thus, the surface preparation by the flushing reagents aids the final placement of the crown.

Figure 1:
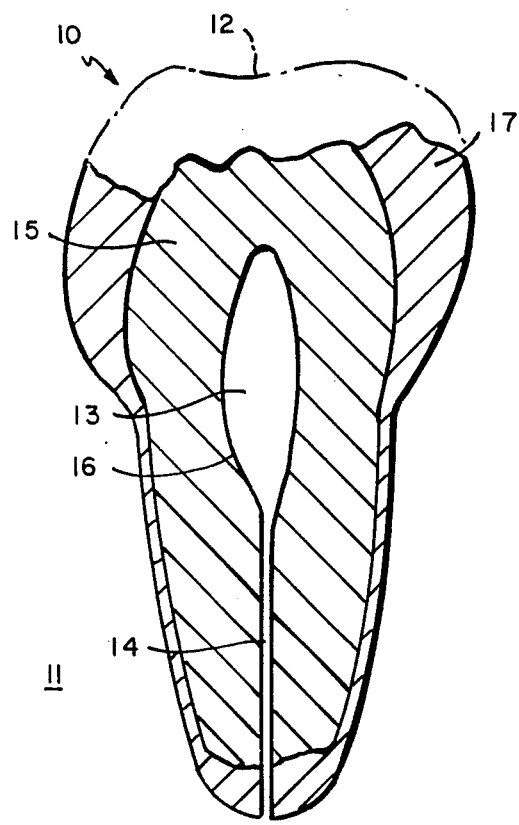
FIG. 1 is a sectional view of a damaged pre-instrumented tooth.

In the drawing, a tooth composed of a crown area 10 and root area 11 is partially illustrated in FIG. 1. The tooth, damaged and missing the coronal portion 12, comprises dentin which surrounds the pulp cavity 13 and its extension, the root canal 14. In the living tooth, the pulp cavity 13 and root canal 14 are filled with fine connective tissue which contains fibroblasts, histiocytes, odontoblasts, blood vessels and nerves. The oldest or primary dentin 15 lies at the periphery of the tooth and the secondary dentin 16 lies along the pulp cavity 14, where it is formed throughout life by odontoblasts. Dentin of the crown area is covered by a thick layer of enamel 17.

Figure 2:
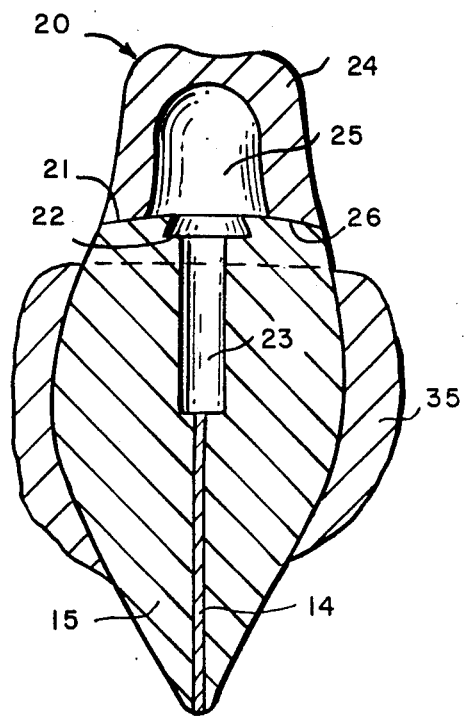
FIG. 2 is a sectional view of an instrumented tooth and prepared crown replacement.

A damaged tooth that has been instrumented and fitted with a preformed coronal replacement 20 is illustrated in FIG. 2. The instrumented tooth resting in gum or gingival tissue 35 comprises an instrumented coronal surface 21, a counterbore 22, and a bore 23. The coronal replacement 20 comprises the replacement shell 24, a post acceptance space 25 and an instrumented replacement surface 26 that substantially contacts the instrumented coronal surface 21.

Figure 3:
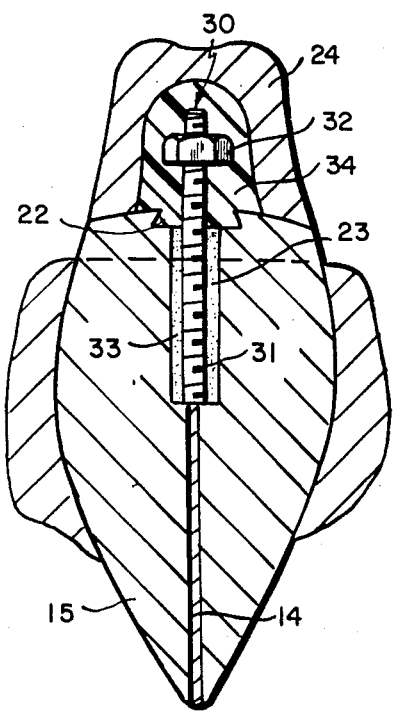
FIG. 3 is a sectional view of an instrumented tooth having a crown replacement.

A tooth having a crown replacement installed is illustrated in FIG. 3 and comprises a bore 23, a counterbore 22, a threaded post 30, the apex of the thread 31 of the post, the threaded nut or fastener 32, cement or a luting agent 33, and a formed core 34.

In accordance with the invention, a foundation of superior tensile strength for a coronal structure is obtained by use of a chelating agent and organic solvent solution to clean the instrumented areas 22 and 23 prior to cementing of a post 30. Preferably, the bore 23 and counterbore 22 are rinsed with a chelating agent prior to a flush with an organic solvent. The luting agent or cement preparation 33 is preferably placed in the bore 23, and the fitted post 30 is seated and held or supported until the cement 33 solidifies. A core 34 is formed around the exposed post 30 and fastener 32 and may be composed of the same or similar cementing medium. Other materials may be used. Following formation of the core 34, the crown replacement 20 is positioned in place.

In the preferred embodiment, the instrumented coronal surface 21 is formed from the damaged tooth. Then, the pulp cavity 13 (and/or the root canal 14, depending on the extent of work) is instrumented to form the bore 23. The depth and diameter of the bore 23 will be influenced by the size of the pulp cavity 13 and the size of the tooth. Preferably, the majority of the root canal filling is removed to expose the dentin and provide a suitable surface to which the cement may adhere. The final shape of the bore is usually substantially cylindrical, however the shape may be other shapes, such as conical or trapezoidal. Since a certain preferred dimension cannot always be obtained for the bore, the long-term integrity of the foundation of the coronal replacement 20 depends upon the adherence of the cement to the instrumented surface.

Preferably, an irrigant is used during instrumentation to aid in removal of material from the pulp cavity 15 and to lubricate the cutting tool prior to the final flush following instrumentation. Commonly used irrigants include sodium hypochlorite (NaOCl) solution, hydrogen peroxide solution, TEGO, REDTA, RC-Prep, polyacrylic acid (20% aqueous solution, 5000 MW) and water. TEGO is a one percent solution of dodecyldiaminoethyl glycine and is available from Goldschmidt Products Corporation, White Plains, N.Y. REDTA is a commercial preparation comprising disodium ethylenediaminetetraacetate (EDTA) 17.00 gm, cetyl trimethylammonium bromide 0.84 gm, 5N sodium hydroxide solution 9.25 ml, distilled water 100 ml, and may be obtained, e.g. from Roth Drug Company, Chicago, Ill. RC-Prep is also a commercial EDTA preparation in a paste form that is used in conjunction with sodium hypochlorite and comprises urea peroxide 10%, EDTA 15%, a water soluble base and may be obtained from Premier Dental Products Co., Philadelphia, Pa. Preferably, NaOCl is administered as the irrigant during instrumentation in an amount that removes a substantial portion of the pulp debris and lubricates the cutting tool, more preferably NaOCl is provided in a solution having a concentration of NaOCl in the range of 1% to 20%, preferably 2–10%, and most preferably in a solution having a concentration of 4.0 to 6.0 percent NaOCl was found to be the most effective solution during instrumentation. All concentrations are by weight unless otherwise noted.

Following instrumentation, the bore 23 is contacted with a chelating agent and with a solvent or dispensant for organic material. Preferably, the bore is contacted with the chelating agent prior to a flush with an organic solvent. The purpose of the chelating agent is to substantially remove the instrumented or smeared layer which is primarily calcific in composition. Suitable chelating agents include but are not limited to EDTA and citric acid. Preferably, EDTA is administered as the chelating agent in an amount that substantially removes the smeared layer, more preferably EDTA is provided in solution having a concentration in the range of 1 percent to 50 percent, and most preferably in a solution having a concentration of 16.0 to 18.0 percent EDTA. The chelating agent and other aqueous materials are preferably buffered to approximate neutrality, e.g. a pH of 7.5. In addition to the concentration of the chelating agent, a minimum volume of the solution must be flushed through the instrumented area to substantially remove the majority of the smeared layer. The volume of chelating agent such as 17% EDTA which may be administered should be sufficient to do the job, and may broadly range from about 1 cc to 300 cc. Preferably, less than 10 cc flush per tooth is used, and often a fluid of 2-3 cc is sufficient.

To obtain maximum effect after instrumentation, the chelating agent should be followed by an organic solvent or dispensant. The chelating solutions alone effectively remove the smeared layer but leave varying amounts of superficial debris, such as tissue and cellular components and possibly bacteria. Suitable organic solvents include but are not limited to, sodium hypochlorite and an ampholytic soap, such as TEGO or other surface active agents, emulsifiers, etc. By "organic solvent" is meant a material which dissolves, dispenses or otherwise chemically removes the organic debris left after instrumentation. Suitable materials are known and described, e.g. in McCutchen's Publications (1981), the disclosure of which is incorporated herein by reference. An ampholytic soap forms both cations and anions and thus may combine the bactericidal activity of cations with the surface tension reduction and solvent actions of anions. Preferably, NaOCl is administered as the organic solvent in an amount that substantially removes the superficial debris. For example, NaOCl may be provided in solution having a concentration in the range of 1% to 20%, preferably about 2.8%, and most preferably in a solution having a concentration of about 4-6%, but most preferably about 5.25% NaOCl, buffered to pH 7.5. In addition to the concentration of the organic solvent, a minimum volume of the solution must be flushed through the instrumented area to substantially remove the majority of the superficial debris. If an organic solvent such as NaOCl is administered, preferably, a volume of NaOCl solution is provided in the range of about 1 cc to 300 cc, more preferably 5 cc to 50 cc, and most preferably about 8.0 to 12.0 cc flush.

Following instrumentation of the bore 23, a counterbore 22 may be instrumented into the substance of the tooth. The purpose of the counterbore 22 would be to provide additional area for adhesion of the cement or a mechanical lock, if shaped appropriately, once the cement hardens. Preferably, the counterbore 22 is formed at the time of the instrumentation of the bore 23 therefore permitting administration of the preferred reagents as irrigant and final flushing agents in the manner described above.

Subsequently, a post 30 is fitted into the bore 23 to provide a mechanical anchor for the coronal replacement 20. The post is preferably available commercially as an endodontic item, more preferably it is manufactured by any conventional process used for making such posts and most preferably it is made of a lightweight material having sufficient compressive strength to withstand the forces generated during mastication and an appropriate coefficient of expansion substantially similar to the companion materials employed for coronal replacement. Posts are generally cylindrical along their long axis and therefore substantially parallel sided, however tapered posts have also been employed in coronal replacement. Post retention is also influenced by shape and surface configuration, e.g., hexagonal or octagonal sides, length, diameter, and presence or absence of serrations, such as threads. The diameter and length of the fitted post are influenced by the size of the bore 23 and the size of the coronal replacement 20. A threaded post may be screwed directly into the bore 23, however, the danger of cracking the tooth is a prominent disadvantage. However, serrated posts, used in conjunction with cement, are more retentive than smooth posts, and the surface configuration is more important than length. Various surface configurations, e.g., threads, serrations, convex protrusions or concave indentations, scales, etc., provide an increased surface area on the exterior of the post. Once the cement has hardened around the post, these surface configurations, such as the apex of a thread 31, provide a significant barrier, e.g., a mechanical lock, to removal of the post from the hardened cement.

Preferably, a post with significant retentive properties such as a substantial gripping surface for the luting agent is employed in this invention to provide an anchor for the coronal replacement, more preferably the post would have significant surface configuration such as serrations, as illustrated in FIG. 3. After the post 30 is attached to the tooth by hardened cement, a fastener 32 is screwed on or otherwise attached to the protruding post to aid in anchoring the core 34.

Figure 4:
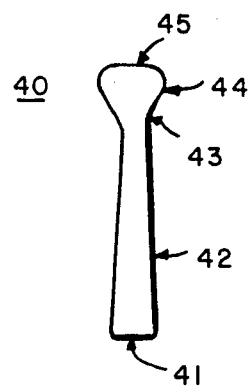
FIG. 4 is a front elevational view of a double-tapered post.

In an alternative embodiment, a substantially cylindrical double-tapered post 40 illustrated in FIG. 4 may be employed as an anchor for a coronal replacement. The one-piece double-tapered post 40 comprises a bottom surface 41, from which the lower tapered portion 42 extends toward the middle section 43. The middle section 43 is necessarily of a lesser diameter than the bottom surface 41 and divides the lower tapered portion 42 from the upper tapered portion 44 and top surface 45. The purpose of the lower tapered portion 42 is to provide a mechanical means of retaining the post in the hardened cement, similar to the function of the threads of the post 30 of the preferred embodiment. The upper tapered portion 44 provides an anchor for the core 34 similar to the function of the threaded fastener 32. The one-piece double-tapered post 40 would preferably be manufactured by any conventional method of a lightweight material having the compression and strength characteristics mentioned above.

Luting or cementing agents are utilized to affix the post 30 to the dentin 15 and may be used to form the core 34 as well. The strength of the foundation is also influenced by the type of cement employed to anchor the post. Commonly available cements for luting preparations include, but are not limited to, zinc oxyphosphate, polycarboxylate, cyanoacrylate and various resins. Preferably, the luting agents employed have substantial adhesive properties and are easily prepared and employed in the method of the invention, more preferably the luting agents have a high compressive strength in the range of 12,000 lb/in$^2$ to 30,000 lb/in$^2$ and tend to resist the tensile and shear forces placed on the material by mastication. Most preferably the luting mixtures of cements have a compressive strength of at least 20,000 lbs/in$^2$. A suitable luting agent is an unfilled resin, Bis-gamma methacrylate (Bis-GMA), combined with the catalyst therefore, which has a compressive strength approaching 20,000–30,000 lbs/in$^2$) and which has a watery consistency, and flows easily with a low surface tension. Thus, these properties enhance its usefulness since it is easily mixed and applied. Preferably, Bis-GMA is applied in solution in a concentration that would provide a compressive strength of at least 12,000 lbs/in$^2$, more preferably at least 20,000 lbs/in$^2$ and most preferably approximately 30,000 lbs/in$^2$.

Once the post 30 has been fitted to the tooth, a quantity of cement 33 sufficient to contact the dentin 15 and the fitted post 30 is deposited in the bore 23. The length of the post is adjusted during fitting so that a portion of the post protrudes from the bore. Once the post is anchored in the hardened cement, the threaded fastener 32 is rotatably attached to the protruding part of the post 30. The threaded fastener 32 is preferably made of a lightweight material having a compressive strength similar to that of the post 30. The purpose of the threaded fastener 32 is to provide a prominent surface around which a core 34 may be formed. This prominent surface and the counterbore may be used together to provide a mechanical means of retaining the core 34 once it has hardened.

The core 34 may be composed of a composite, cement or luting agent similar to the core cement, or a different substance, such as amalgam. Preferably, the core 34 should be composed of a material having sufficient bonding and compressive strength to withstand the pressures encountered. In addition, the core substance must have substantial mechanical and/or chemical affinity for the coronal replacement 20.

The coronal replacement 20 is preferably preformed by any manufacturing process used in molding crowns, and comprises a replacement shell 24 and a post acceptance space 25. During the fitting procedure the coronal replacement 20 is substantially shaped to create an instrumented replacement surface 26 which conforms to the contours of the instrumented coronal surface 21. Once the coronal replacement 20 has been fitted to the tooth, a core 34 is formed around the threaded fastener 32 and post 30 providing an amount of core substance to substantially fill the counterbore 22 and post acceptance space 25 of the coronal replacement 20.

Although not wishing to be bound by theory as to why the structure prepared by this invention reduces the possibility of loosening, it is believed that when the organic debris and the smeared layer are removed from the machined bore 23 and counterbore 22, the dentinal tubules are exposed. The most effective final flush after instrumentation was found to be 10 cc of 17 percent EDTA followed by 10 cc of 5.25 percent NaOCl. The best result is obtained when a 5.25 percent solution of NaOCl is employed during instrumentation to lubricate and remove the majority of the pulp debris. Thus, a cementing medium which has great compressive strength such as Bis-GMA resin can flow into the open tubules and into the serrations of the post and provide greatly enhanced tensile strength.

The following examples are set forth to further illustrate the present invention.

PREPARATION AND ANALYSIS OF MATERIALS

One hundred and twenty freshly extracted singly-rooted teeth were selected. The crowns were removed at the cervical line and a post preparation either 4 mm or 7 mm was made with the appropriately sized burr to receive a 0.050 parapost (Whaledent Corp.). The teeth were then divided into two groups of 60 teeth each. Each group was further subdivided into two groups, each of which had 30 teeth with 4 mm preparations and 30 teeth with 7 mm preparations.

In Group A, all the post preparations were flushed with a syringe and 23 gauge needle using 2 cc of 5.25% NaOCl and the canals were dried with paper points and air. In Group B, all the post preparations were flushed with a syringe and 23 gauge needle using 1 cc of 17% EDTA solution followed by 1 cc of 5.25% NaOCl after which the canals were dried with paper points and air. Both groups were then divided into three subgroups (Table I).

Group A—all teeth flushed with 2 cc of 5.25% NaOCl and dried with an air blast and paper points.

Group A 1—Zinc oxyphosphate cement powder and liquid were dispensed onto the clean, dry surface of a glass slab and carefully mixed according to manufacturer's directions to a creamy consistency suitable for cementation. A lentulo spiral was used to place the cement in each post preparation. The post was then coated with the cement and seated to place and held until initial setting occurred.

Group A 2—Polycarboxylate cement powder and liquid (Durelon-Premier) were dispensed onto a clean dry slab and carefully mixed according to manufacturer's directions to a creamy consistency. A lentulo spiral in a suitable handpiece was used to place the cement in the post preparation. The post was coated with the cement and seated to place and held until initial setting occurred.

Group A 3—A 30% mixture of Bis-GMA resin with the catalyst, TEGDMA, was dispensed onto a paper mixing pad, the catalyst added and mixed. A lentulo spiral by hand was used to place the resin in the post preparation until it was completely coated. Resin was used to coat the post which was seated and held until initial set.

Group B—all teeth were flushed with 1 cc of 17% EDTA followed by 1 cc of 5.25% NaOCl and then dried with an air blast followed by paper points.

Group B 1—Posts cemented with zinc oxyphosphate cement and same procedure as Group A 1.

Group B 2—Posts cemented with polycarboxylate cement and same procedure as Group A 2.

Group B 3—Posts cemented with unfilled Bis-GMA resin and same procedure as Group A 3.

After cementation, all teeth were stored in 100% humidity at room temperature for at least one week before testing.

The teeth were then tested for tensile strength on an Instron testing machine at a cross head speed of 0.1 in/min. The tensile strength of the post was tested to failure.

The results were statistically analyzed using a 3-dimensional factorial analysis of variance. Results were obtained for 114 teeth. The tensile strength s are summarized in Table I.

Without wishing to be bound by theory, it is believed that the improvement obtained by use of the particular solvent combination, removes both the organic and inorganic debris, and thus eradicates the smeared layer which would otherwise overlay the tubules. With this layer removed a light, low viscosity, low surface tension like unfilled gamma methacrylate can penetrate these pores, thus to establish a mechanical seal in which the cured resin protrudes into the pores and sets up a mechanical lock inside the tubules. The strength of this bond is believed to be such that bond failure generally occurs within the adhesive itself, rather then to the interface.

TABLE I

Relative Tensile Strength of Posts Using Different Binding Agents and Different Resins

|  | NaOCl | EDTA & NaOCl | Recent Improvement |
|---|---|---|---|
| Group I - 4 mm. Posts |  |  |  |
| Zinc phosphate | 37.59 | 52.73 | 40% |
| Polycarboxylate | 29.03 | 40.05 | 38% |
| Resin | 51.55 | 97.40 | 89% |
| Group II - 7 mm. Posts |  |  |  |
| Zinc phosphate | 51.31 | 63.40 | 24% |
| Polycarboxylate | 41.55 | 46.37 | 12% |
| Resin | 55.00 | 124.20 | 126% |

The very clear cut superiority of the posts cemented with Bis-GMA resin following an EDTA-NaOCl flush was indisputable. As shown in Title I, it was significantly better in every case and under every circumstance. The strongest post in the zinc phosphate group was the 7 mm one following the EDTA-NaOCl rinse. The 4 mm post cemented with Bis-GMA after an EDTA-NaOCl rinse had an 89% improvement in tensile strength, as compared with the same post and resin, but utilizing only an NaOCl resin. The 7 mm post cemented with Bis-GMA after an EDTA-NaOCl rinse had more than twice the tensile strength. The strongest post in the polycarboxylate group was the 7 mm one cemented after an EDTA-NaOCl flush and here the 4 mm Bis-GMA post was twice as strong and the 7 mm Bis-GMA post was three times as strong.

These results indicate that when the smeared layer is removed and the dentinal tubules are exposed, a cementing medium which has great compressive strength such as the Bis-GMA resin which is not soluble in the oral fluids, can flow into the open tubules on the one side and into the serrations of the post on the other side can provide a greatly enhanced tensile strength.

An important aspect of this technique lies also in the fact that since a 4 mm post cemented with the unfilled Bis-GMA following an EDTA-NaOCl rinse, can have one and a half times the tensile strength of the best 7 mm post cemented with zinc phosphate, shorter posts can and should be used. These are much easier to prepare and inadvertant perforations of the side of slender or curved roots would be much less likely to occur. If a longer post is chosen, then the 7 mm post cemented with unfilled resin after an EDTA-NaOCl rinse has tensile strength equalling or at least approaching the tensile strength of known screw-in posts. This allows a simpler procedure without the danger of cracking the root which is inherent with the screw-in post.

When the invention is used to provide a foundation for a coronal structure, the danger of the core loosening or being damaged due to the tremendous pressure encountered by the dental structure is significantly reduced. Reduction of loosening problems will be effected by using any preparation in accord with the invention having a prepared dental area flushed by a chelating agent followed by an organic solvent and a luting agent of high compressive strength employed to anchor a post inserted therein for a coronal structure.

Additional advantages and modifications will readily occur to the skilled in the art upon consideration of this disclosure. Accordingly, departure may be made from the detail without departing from the spirit or scope of the disclosed general inventive concept.

I claim:

1. Kit for use in restructuring a tooth, comprising complete instructions for using the components contained therein said components consisting of sequentially in order of use at least one plugger to heat and remove gutta percha, at least one burr to prepare a site consisting of a bore and counterbore, at least one drill for final preparation of the bore, at least one post corresponding in size to the drill, a chelating reagent for flushing the site, an organic solvent reagent for flushing the site after the reagent flushing, a cementing medium consisting of an unfilled resin and catalyst for application to the site within which the post is seated, a spiral apparatus for the said application of cementing medium in the prepared site, and a composite resin to fabricate a core and a crown form around the post.

2. Kit of claim 1 wherein said chelating reagent is EDTA.

3. Kit of claim 1 wherein EDTA is provided in a 1–50% solution buffered to PH of about 7.5.

4. Kit of claim 1 wherein said organic solvent is sodium hypochlorite.

5. Kit of claim 4 wherein sodium hypochlorite is provided in a 5.25% solution buffered to PH 7.5, in a volume of 10 cc.

6. Kit of claim 1 wherein said unfilled resin is Bis-GMA.

7. Kit of claim 1 wherein said unfilled resin catalyst is TEGDMA.

8. Kit of claim 1 wherein said spiral apparatus are Lentulo Spirals selected from a plurality of sizes.

9. Kit of claim 1 wherein said composite is a resin.

10. Kit of claim 1 wherein said crown form is celluloid.

11. Kit of claim 1 wherein said crown form is plastic.

12. Kit of claim 1 wherein an irrigation substance is provided.

13. Kit of claim 12 wherein said irrigation substance is NaOCl.

* * * * *